(12) United States Patent
McKelvey

(10) Patent No.: US 12,203,915 B2
(45) Date of Patent: Jan. 21, 2025

(54) SYSTEM FOR MONITORING WATER QUALITY

(71) Applicant: OzGreen Energy Pty Ltd, Parkwood (AU)

(72) Inventor: Len McKelvey, Parkwood (AU)

(73) Assignee: OzGreen Energy Pty Ltd, Parkwood (AU)

( * ) Notice: Subject to any disclaimer, the term of this patent is extended or adjusted under 35 U.S.C. 154(b) by 548 days.

(21) Appl. No.: 17/428,248

(22) PCT Filed: Feb. 4, 2020

(86) PCT No.: PCT/AU2020/050073
§ 371 (c)(1),
(2) Date: Aug. 3, 2021

(87) PCT Pub. No.: WO2020/160599
PCT Pub. Date: Aug. 13, 2020

(65) Prior Publication Data
US 2022/0229038 A1 Jul. 21, 2022

(30) Foreign Application Priority Data
Feb. 4, 2019 (AU) .................................. 2019900331

(51) Int. Cl.
*G01N 33/18* (2006.01)
*G01N 1/18* (2006.01)
(Continued)

(52) U.S. Cl.
CPC ........... *G01N 33/1886* (2013.01); *G01N 1/18* (2013.01); *G01N 1/2035* (2013.01); *G01K 13/12* (2013.01)

(58) Field of Classification Search
CPC .... G01N 33/1886; G01N 1/18; G01N 1/2035; G01N 33/18; G01N 2001/021;
(Continued)

(56) References Cited

U.S. PATENT DOCUMENTS 3,913,384 A   10/1975 Furuya et al.
7,219,553 B1 *  5/2007 Worthington ............. F17D 5/02
                                                     73/753

(Continued)

FOREIGN PATENT DOCUMENTS

CN   207516352 U   6/2018
CN   207528273 U   6/2018
(Continued)

OTHER PUBLICATIONS

European Search Report for Application No. 20753203.7-1001 dated Mar. 9, 2022.
(Continued)

*Primary Examiner* — Lisa M Caputo
*Assistant Examiner* — Joshua L Forristall
(74) *Attorney, Agent, or Firm* — Jordan IP Law, LLC

(57) ABSTRACT

A lid mounted water sampling system adapted to be fluidly coupled to a water line for obtaining water quality parameters corresponding to a sample of pressurized water from the water line and transmitting information associated with said water quality parameters to a remote location, the system comprising: a pit lid adapted to be positioned to cover a pit box such that during use an outer surface of the pit lid is substantially at ground level and adapted to be positioned upon the pit box located underground; the pit lid further comprising an in-use underside portion coupled to a water sampling apparatus, the water sampling apparatus adapted to be positioned in an internal volume defined by the pit box, the water sampling apparatus being fluidly coupled
(Continued)

to the water line for obtaining water quality parameters corresponding to a sample of the pressurized water from the water line; and a data transmitter positioned adjacent said pit lid in electronic communication with the water sampling apparatus for transmitting the water quality parameters to the remote location.

22 Claims, 11 Drawing Sheets

(51) Int. Cl.
  *G01N 1/20* (2006.01)
  *G01K 13/12* (2006.01)
(58) Field of Classification Search
  CPC ..... G01N 2001/105; G01N 2001/2064; G01N 33/1813; G01N 33/1826; G01K 13/12; E03B 7/07; E03B 7/075; E03B 7/078; G01M 3/2815; G01L 19/0618
  See application file for complete search history.

(56) References Cited

U.S. PATENT DOCUMENTS

| | | | |
|---|---|---|---|
| 10,226,722 B1 * | 3/2019 | Baird | .................. B01D 35/143 |
| 2004/0079689 A1 | 4/2004 | Newman | |
| 2007/0163334 A1 * | 7/2007 | Boyd | .................. G01N 1/2035 73/756 |
| 2009/0123340 A1 * | 5/2009 | Knudsen | .............. G08B 21/182 73/61.41 |
| 2010/0132440 A1 | 6/2010 | Boyd | |
| 2016/0356755 A1 | 12/2016 | Gifford et al. | |
| 2018/0202890 A1 | 7/2018 | Mutch et al. | |

FOREIGN PATENT DOCUMENTS

| | | | | |
|---|---|---|---|---|
| CN | 207964806 U | | 10/2018 | |
| DK | 201670584 A | * | 2/2018 | ............. A01K 61/10 |
| JP | 2006167654 | | 6/2006 | |
| JP | 2006167654 A | * | 6/2006 | |
| WO | 2013006280 | | 1/2013 | |
| WO | WO-2013006280 A1 | * | 1/2013 | ............... B67D 7/22 |
| WO | 2016197096 A1 | | 12/2016 | |

OTHER PUBLICATIONS

International Search Report and Written Opinion for Application No. PCT/AU2020/050073 dated May 19, 2020.
International Preliminary Report on Patentability for Application No. PCT/AU2020/050073 dated Sep. 15, 2020.
Chinese Office Action for Application No. 202080026451.6 dated Jul. 6, 2023.
Indian Examination Report for Application No. 202147035139 dated Feb. 15, 2023.

* cited by examiner

SYSTEM FOR MONITORING WATER QUALITY

TECHNICAL FIELD

The present invention relates a water sampling and testing system for testing water quality.

BACKGROUND

Any references to methods, apparatus or documents of the prior art are not to be taken as constituting any evidence or admission that they formed, or form part of the common general knowledge.

It is important to monitor the quality of water flowing through the water supply lines (often referred to as "water mains") from time to time to ensure that the water is fit for human consumption. One of the conventional ways of monitoring the water quality is to send a technician to a specific water monitoring location. The technician accesses the water supply and collects water samples which are sent to a laboratory for detailed analysis. Once the results become known, the water supplying facility may need to undertake specific action to address any issues with the water quality. One of the issues with such a testing method is that testing cannot be carried out in real time and often the problem with the water quality persists for a long period of time before any potential issues are addressed.

In some instances, the technicians may carry portable testing equipment which consists of portable sampling equipment that is taken from job to job. Once again, the portable testing equipment is only suitable for carrying out "one-off" tests and fails to monitor water quality (including variations in water quality) over a prolonged time period in the order of days or months in a continuous manner.

Installation of water quality monitoring equipment that can monitor water quality over longer periods of time is challenging because such equipment is relatively expensive and installation of water quality monitoring equipment often needs to be undertaken in public spaces. As a result, such equipment is prone to vandalism and may even be stolen. Furthermore, such equipment usually operates in an autonomous manner and any operational changes usually require a technician to physically visit the installation and site and deploy changes which also presents unique operational challenges.

In view of the above, it would be desirable to address some of the issues of the prior art and provide an improved system for monitoring water quality.

SUMMARY OF INVENTION

In one aspect, the invention provides a lid-mounted water sampling system adapted to be fluidly coupled to a water line for obtaining water quality parameters corresponding to a sample of pressurized water from the water line and transmitting information associated with said water quality parameters to a remote location, the system comprising:
  a pit lid adapted to be positioned to cover a pit box such that during use an outer surface of the pit lid is substantially at ground level and adapted to be positioned upon the pit box located underground;
  the pit lid further comprising an in-use underside portion coupled to a water sampling apparatus, the water sampling apparatus adapted to be positioned in an internal volume defined by the pit box, the water sampling apparatus being fluidly coupled to the water line for obtaining water quality parameters corresponding to a sample of the pressurized water from the water line; and
  a data transmitter positioned adjacent said pit lid in electronic communication with the water sampling apparatus for transmitting the water quality parameters to the remote location.

In an embodiment, the lid-mounted water sampling system further comprises: one or more connectors, preferably quick-coupling connectors, for coupling the water sampling apparatus to the water line such that the lid-mounted water sampling system is adapted to be readily uncoupled from the water line.

In an embodiment, the water sampling apparatus is adapted to measure one or more of the following parameters: (a) transient pressure; (b) temperature of water; (c) pH of water; (d) oxidation reduction potential (ORP); (e) Conductivity ($E_C$) (f) Free Chlorine concentration.

In further embodiments, the system may also measure one or more of the following parameters: hypochlorous-acid concentration; disinfectant residual; TC concentration; turbidity; Total Organic Carbon concentration; Total Chlorine concentration; Combined Chlorine concentration; Hydrogen Peroxide concentration.

In an embodiment, the lid-mounted water sampling system further comprises: a first sampling line for being coupled with the water line for allowing flow of water from the water line to a dynamic pressure detector to measure the transient pressure in the water line; and a second sampling line for being coupled with the water line for allowing flow of water from the water line to a plurality of sampling chambers with corresponding sampling probes, the sampling probes being adapted to sample water quality parameters of a sample of water flowing into said sampling chambers.

In an embodiment, the dynamic pressure sensor is arranged to conduct an initial water sampling step to identify transient pressure in the pipeline and transmitting transient pressure related information to a receiver and a signal processor, said signal processor being arranged to receive and process transient pressure related information to determine if transient pressure in the pipeline satisfies a pre-determined criteria, the signal processor being in communication with a control unit to undertake one or more additional water sampling steps when the pre-determined criteria is satisfied.

In an embodiment, the control unit is arranged to operate the water sampling system in a low power consumption operating configuration when the pre-determined criteria is not satisfied.

In an embodiment, the control unit is programmed or programmable to increase water sampling rates or data recording rates when the predetermined criteria is not satisfied.

In an embodiment, the water sampling apparatus further comprises a sampling valve to control the flow of water from the water line into the first and second sampling lines.

In an embodiment, the sampling valve is in electrical communication with a data trans-receiver for allowing remote actuation of the sampling valve.

In an embodiment, the sampling valve is in electrical communication with a processor to execute sampling instructions written onto a non-volatile memory device arranged in communication with a processor by actuating said sampling valve in accordance with said sampling instructions.

In an embodiment, the water sampling apparatus further comprises a pressure reduction valve positioned in fluid communication with the second sampling line for reducing pressure of water flowing from the water line into the plurality of water sampling chambers.

In an embodiment, the transmitter further comprises an antenna element secured relative to the pit lid wherein a top portion of the antenna element is positioned adjacent to the underside of pit lid for transmitting information associated with said water quality parameters to the remote location.

In an embodiment, the data transmitter for transmitting the water quality parameters to a remotely located processing unit is configured to receive and process the water quality parameters for the one or more samples sampled by the sampling apparatus in accordance with one or more water quality parameters processing instructions written onto a remotely located non-volatile memory unit in communication with said remotely located processing unit.

In an embodiment, the data transmitter is adapted to be in wired or wireless communication with a remote server.

In an embodiment, the water sampling system further comprises a frame assembly for mounting the water sampling apparatus in the underside portion of the pit lid, the frame assembly being coupled to the underside of the pit lid.

In an embodiment, the water sampling system in accordance with any one of the preceding claims further comprising an on-board processing unit in communication with the water sampling apparatus and the data transmitter for processing and transmitting information associated with said water quality parameters to the remote location.

In another aspect, the invention provides a lid-mounted water sampling system comprising: an enclosure for enclosing at least a part of a water sampling apparatus with a sealing arrangement positioned along or adjacent an underside portion of a pit lid adapted to be positioned to cover a pit box, the sealing arrangement being provided to form a seal between the enclosure and the pit lid and/or the water sampling apparatus.

In an embodiment, the sealing arrangement is located at an in-use upper section of the enclosure that forms the seal between the enclosure and the pit lid and/or the water sampling apparatus.

In an embodiment, the enclosure in combination with the water sampling apparatus and/or the pit lid is negatively buoyant to prevent the combination of the pit lid, water sampling apparatus and the enclosure from becoming buoyant when submerged in water.

In an embodiment, the enclosure further comprises an outlet opening to allow water from inside the enclosure to be discharged outside the enclosure.

In an embodiment, the outlet is positioned in an in-use lower section of the enclosure.

In an embodiment, the enclosure comprises a base forming the in-use lower section of the enclosure with upstanding walls extending from the base in a direction towards the pit lid, the outlet being positioned in the base of the enclosure.

In an embodiment, the water sampling system further comprises a sampling pressure regulator to regulate the pressure of water flowing through the water sampling apparatus to be above 101 kilopascals and preferably in the range of 130 kilopascals and 210 kilopascals.

The invention is in no way limited to a lid-mounted water sampling system. In another aspect, the invention provides a water sampling system adapted to be fluidly coupled to a water line for obtaining water quality parameters corresponding to a sample of pressurized water from the water line and transmitting information associated with said water quality parameters to a remote location, the system comprising:

a water sampling apparatus adapted to be positioned below an underside portion of a pit lid within an internal volume defined by a pit box, said pit lid being adapted to be positioned to cover the pit box such that during use an outer surface of the pit lid is substantially at ground level and adapted to be positioned upon the pit box located underground;

the water sampling apparatus being fluidly coupled to the water line for obtaining water quality parameters corresponding to a sample of the pressurized water from the water line; and a data transmitter positioned adjacent said pit lid in electronic communication with the water sampling apparatus for transmitting the water quality parameters to the remote location.

In another aspect, the invention provides a method of sampling water, the method comprising the steps of:

positioning a water sampling apparatus below an underside portion of a pit lid, the pit lid being adapted to be positioned to cover a pit box such that during use an outer surface of the pit lid is substantially at ground level and adapted to be positioned upon the pit box located underground;

fluidly coupling said water sampling apparatus to sample pressurised water from a water line for obtaining water quality parameters corresponding to a sample of the pressurized water from the water line;

transmitting the water quality parameters, by a data transmitter positioned adjacent said pit lid, to a remote location.

In an embodiment, the method comprises the step of measuring one or more of the following parameters:
(a) transient pressure;
(b) temperature of water;
(c) pH of water;
(d) oxidation reduction potential (ORP);
(e) Conductivity ($E_C$)
(f) Free Chlorine concentration.

In an embodiment, the method comprises the steps of: coupling a first sampling line with the water line for line for allowing flow of water from the water line to a dynamic pressure detector and measuring the transient pressure in the water line; and coupling a second sampling line with the water line for allowing flow of water from the water line to a plurality of sampling chambers with corresponding sampling probes, sampling the water flowing into the sampling chambers to sample water quality parameters.

In an embodiment, the method comprises the step of activating a sampling valve arranged to be in fluid communication with the first and second sampling lines, the sampling valve being in electrical communication with a processor to execute sampling instructions written onto a non-volatile memory device by actuating said sampling valve in accordance with said sampling instructions.

In an embodiment, the method comprises the steps of transmitting the water quality parameters to a remotely located processing unit, by using the transmitter, processing the water quality parameters for the one or more samples sampled by the sampling apparatus, by using the processing unit, in accordance with one or more water quality parameters processing instructions written onto a non-volatile memory device in communication with said processing unit.

In an embodiment, the method comprises conducting an initial water sampling step to identify transient pressure in the pipeline by using a dynamic pressure sensor and transmitting transient pressure related information to a receiver and a signal processor, said signal processor being arranged to receive and process transient pressure related information by determining if transient pressure in the pipeline satisfies a pre-determined criteria and in response communicating signals to a control unit to undertake one or more additional water sampling steps when the pre-determined criteria is satisfied.

In an embodiment, the method further comprises the step of operating the water sampling system in a low power consumption operating configuration when the pre-determined criteria is not satisfied.

In an embodiment, the method further comprises the step of increasing water sampling rates or data recording rates when the predetermined criteria is not satisfied.

BRIEF DESCRIPTION OF THE DRAWINGS

Preferred features, embodiments and variations of the invention may be discerned from the following Detailed Description which provides sufficient information for those skilled in the art to perform the invention. The Detailed Description is not to be regarded as limiting the scope of the preceding Summary of the Invention in any way. The Detailed Description will make reference to a number of drawings as follows.

DETAILED DESCRIPTION OF PREFERRED EMBODIMENTS

Figure 1:
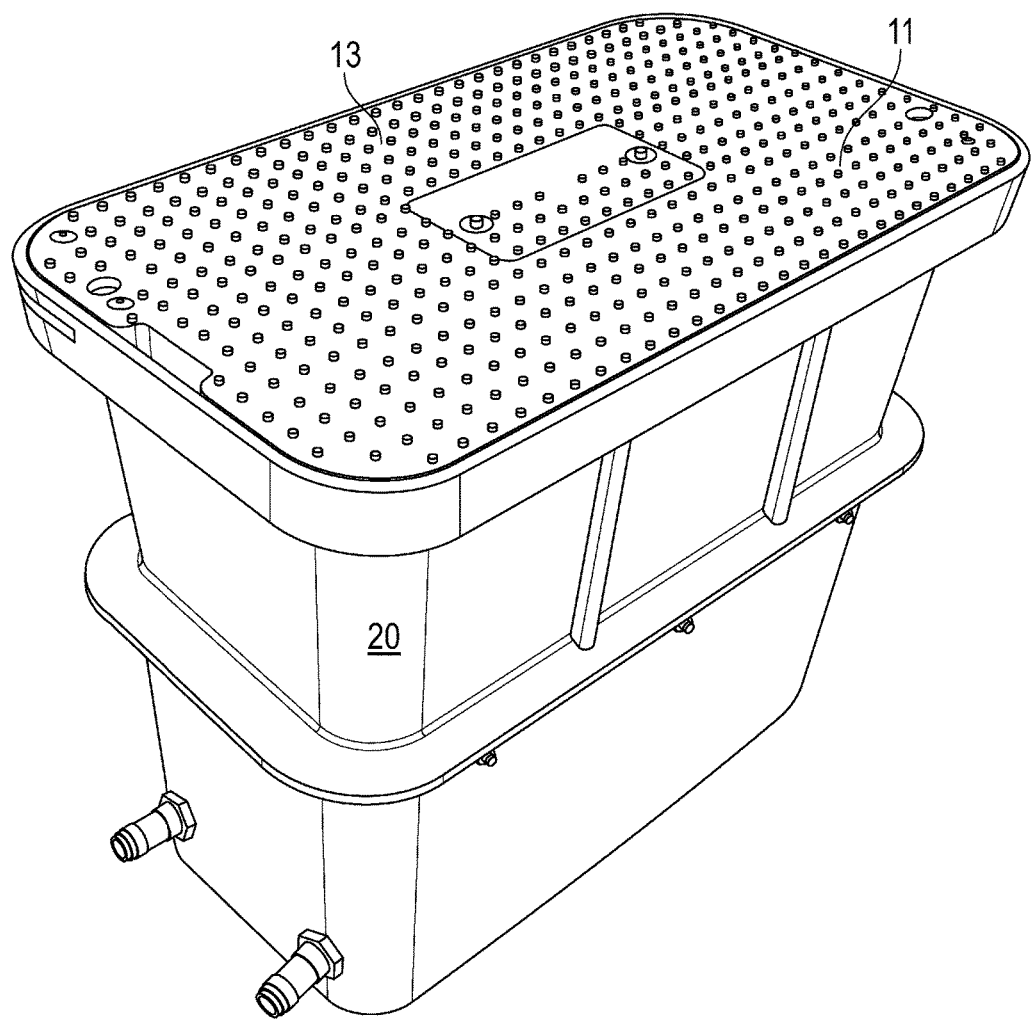
FIG. 1 is a perspective in-use view of the lid mounted water sampling and testing system 10 in accordance with an embodiment of the present invention.
Figure 2:
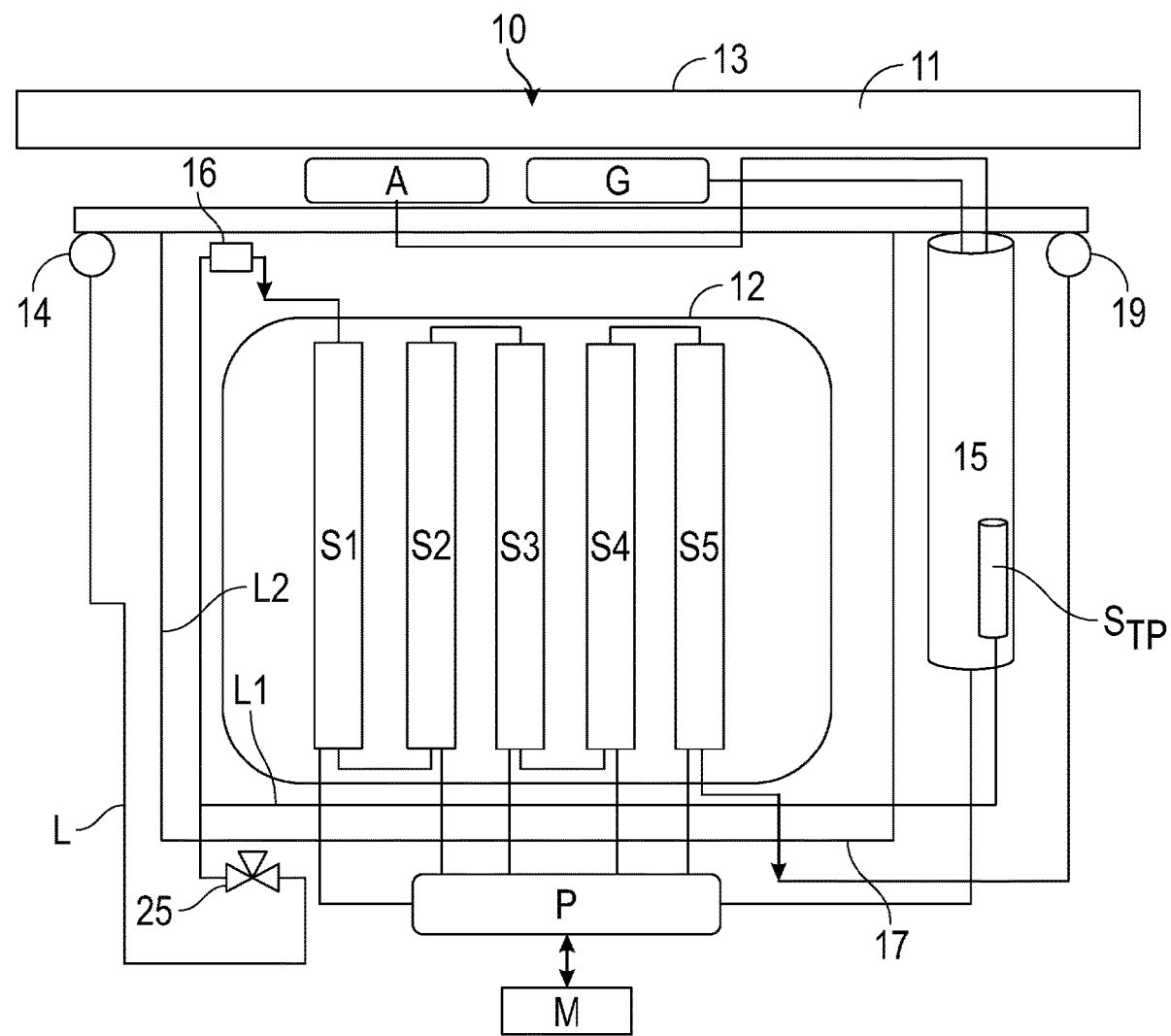
FIG. 2 is a schematic sectional view of the lid mounted water sampling and testing system 10.
Figure 3:
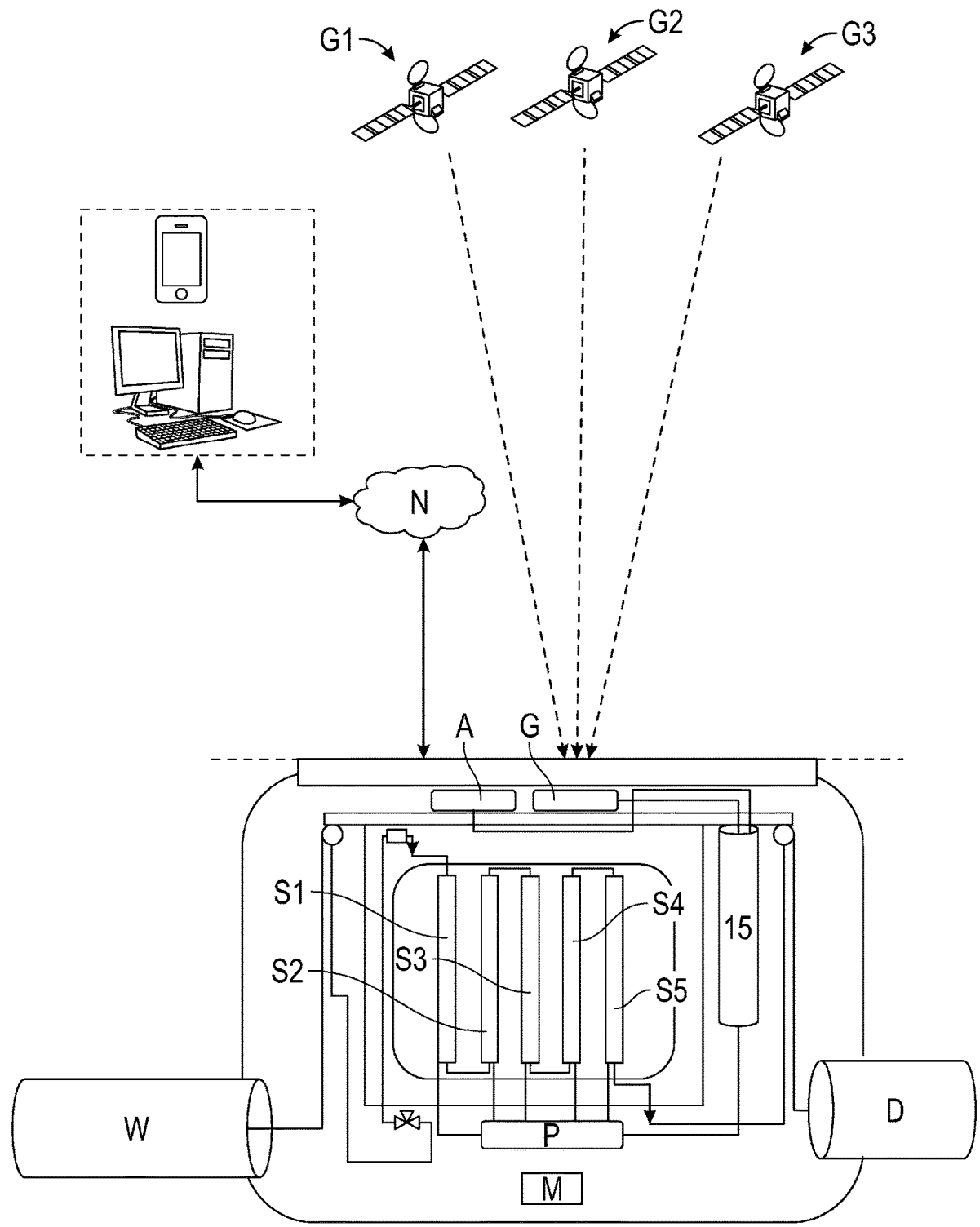
FIG. 3 is a schematic view of a water sampling and testing system 10 in communication with remotely located computing devices over network N.
Figure 4:
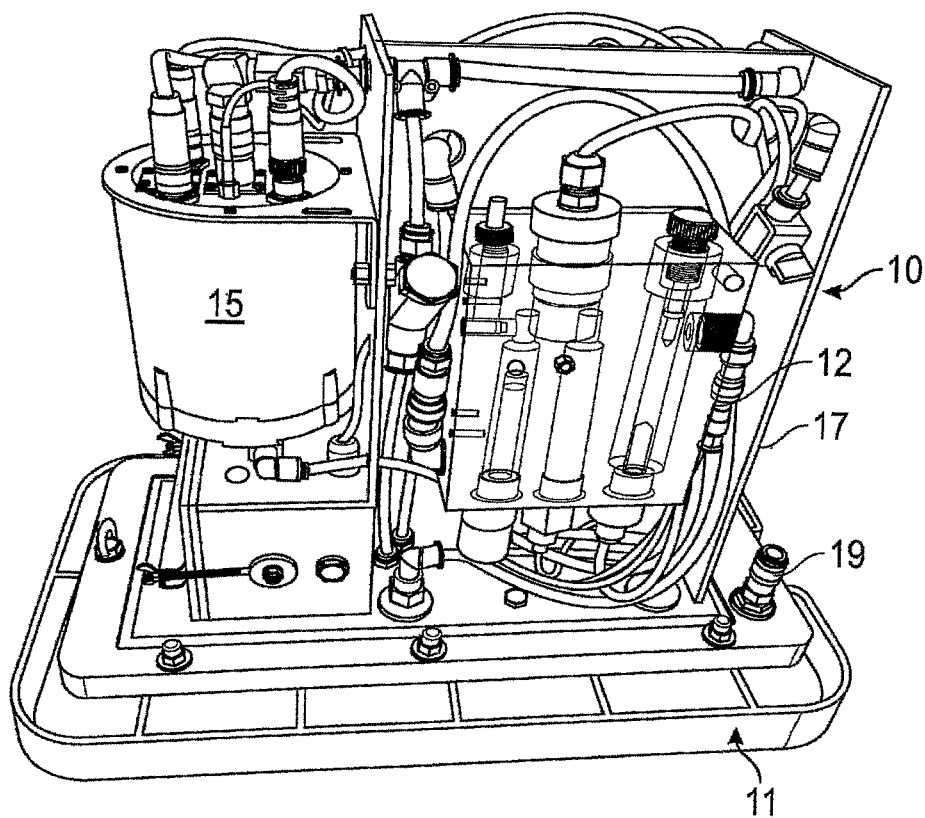
FIG. 4 is an underside perspective view of the water sampling and testing system 10.
Figure 5:
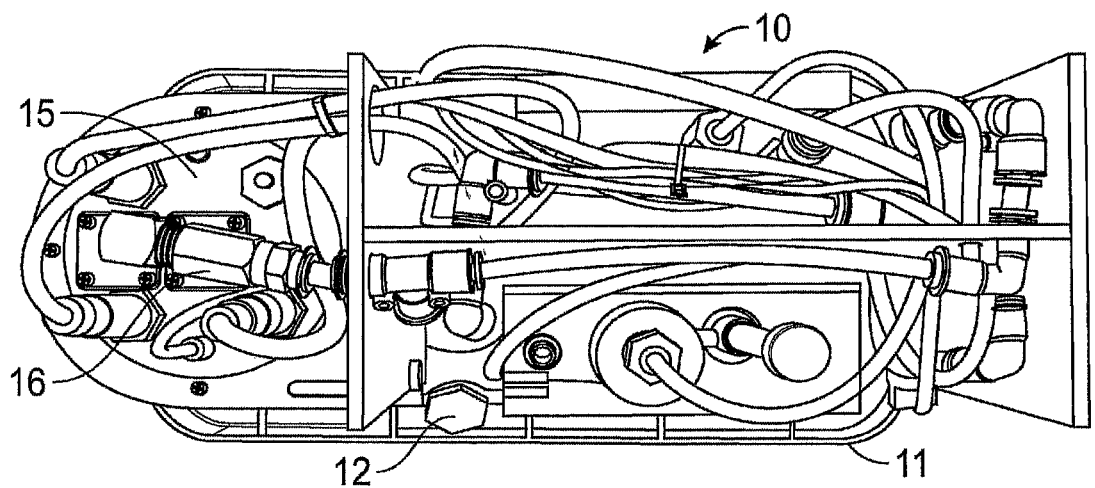
FIG. 5 is an underside bottom view of the water sampling and testing system 10.
Figure 6:
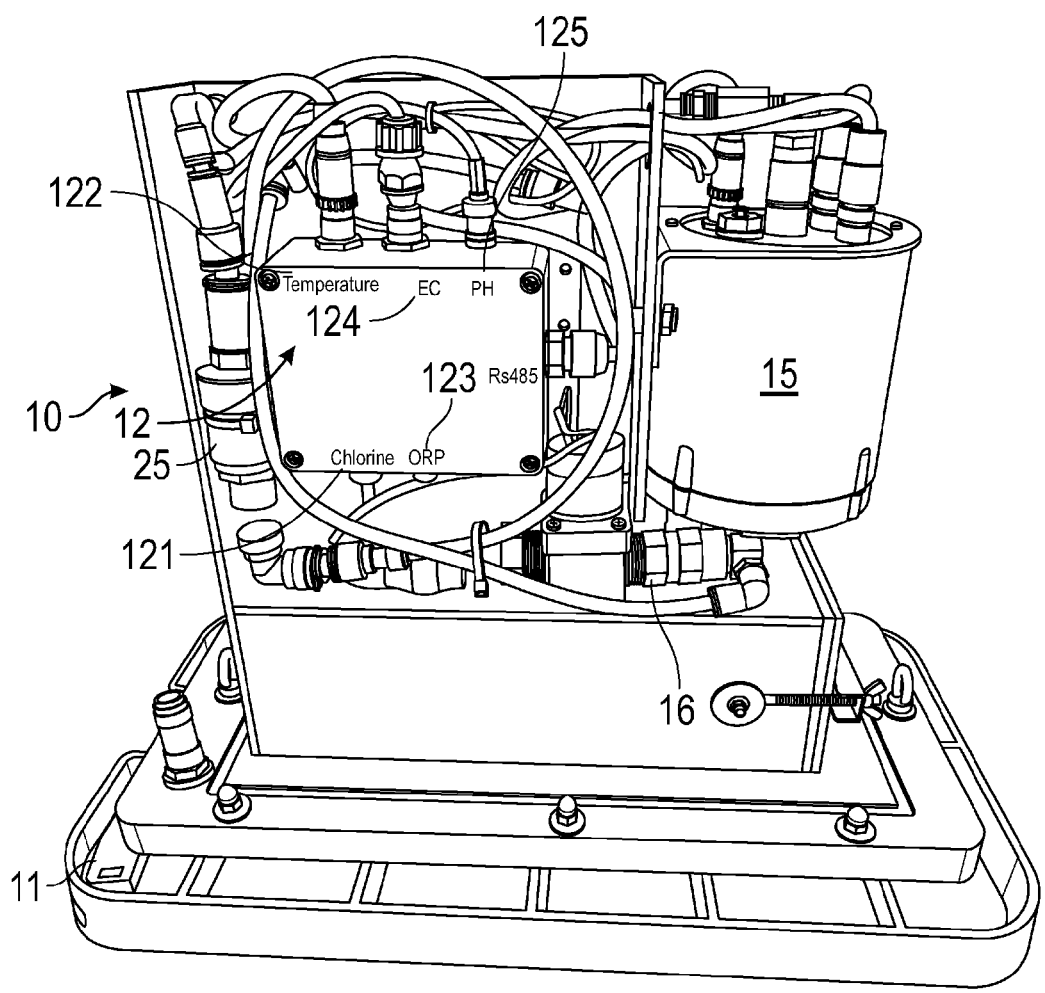
FIG. 6 is an enlarged side view of the water sampling and testing system 10.
Figure 7:
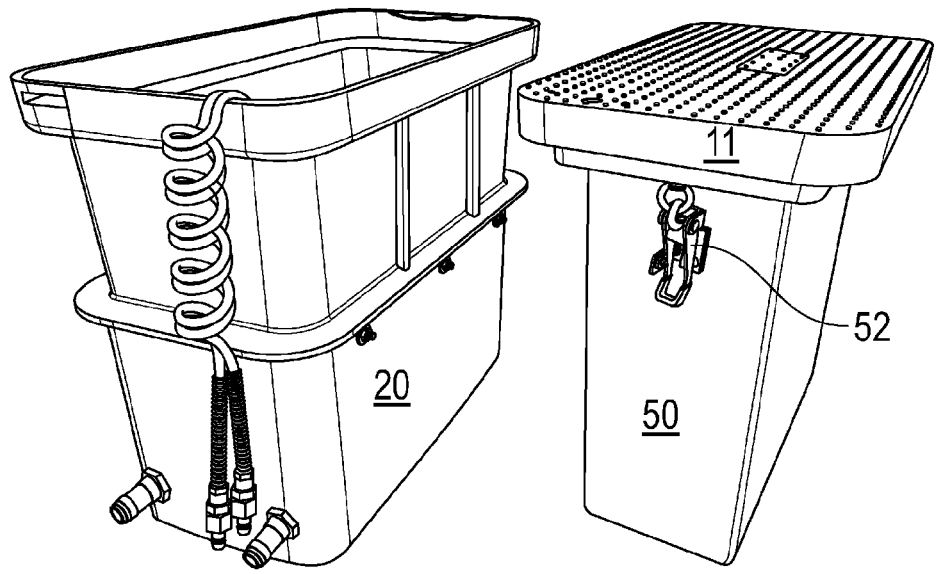
FIG. 7 is an underside perspective view of the water sampling and testing system 10 and the pit box 20.
Figure 8:
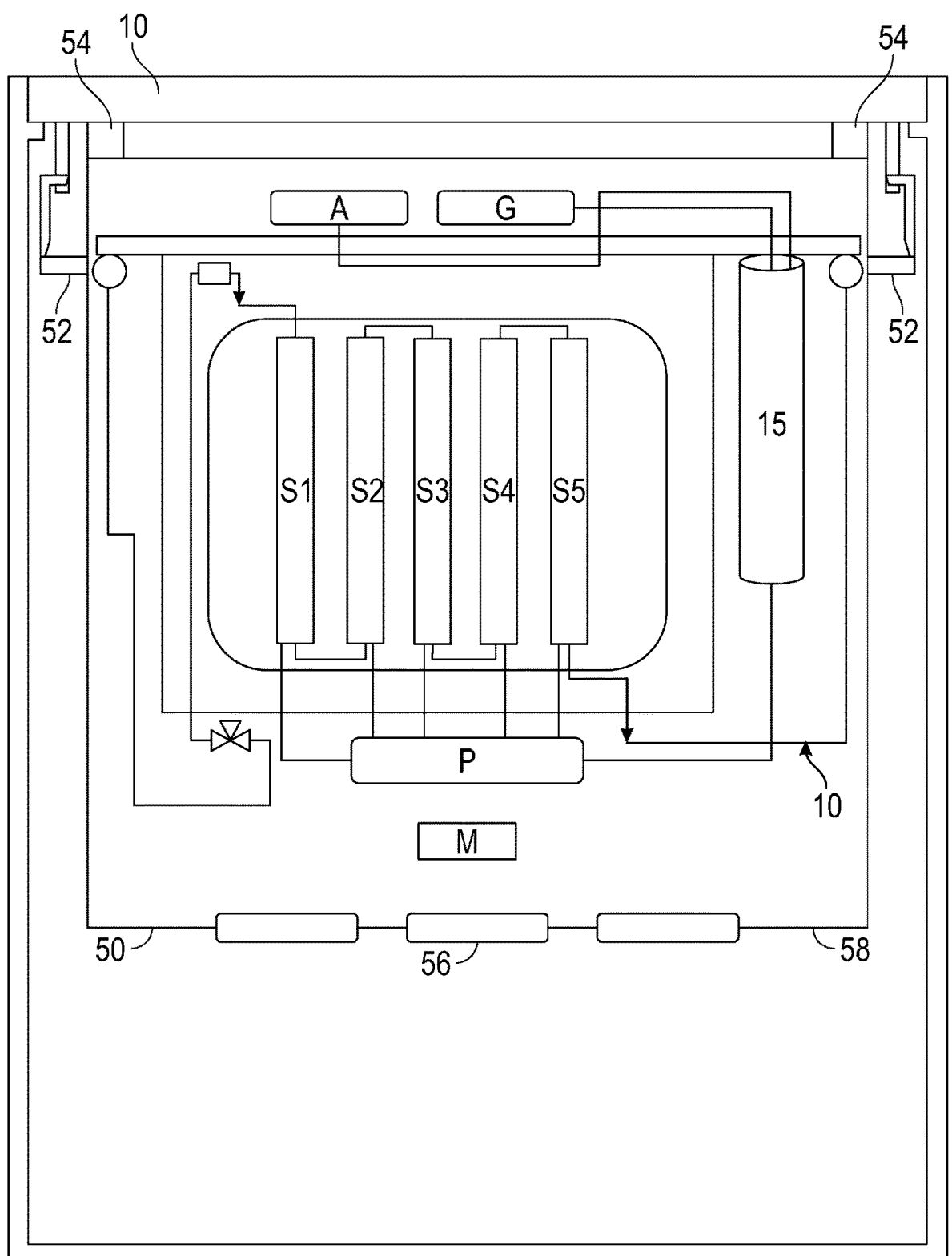
FIG. 8 is a side view of the water sampling and testing system 10 housed within a sealed enclosure 50 as positioned within the pit box 20.
Figure 9:
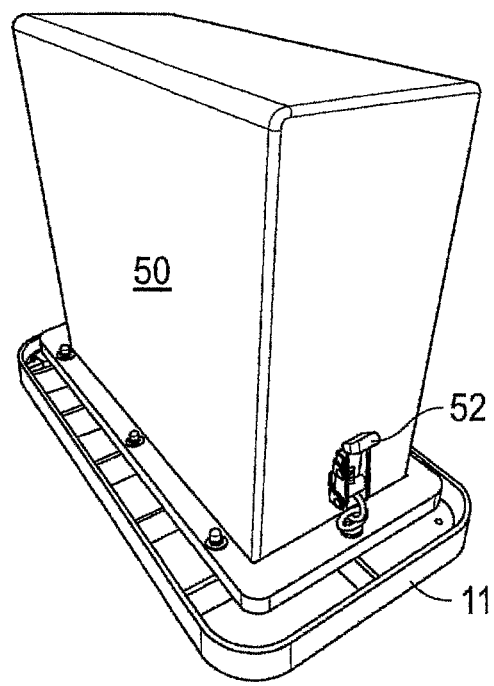
FIG. 9 is an underside view of the enclosure 50 shown in a sealed configuration with the pit lid 11.
Figure 10:
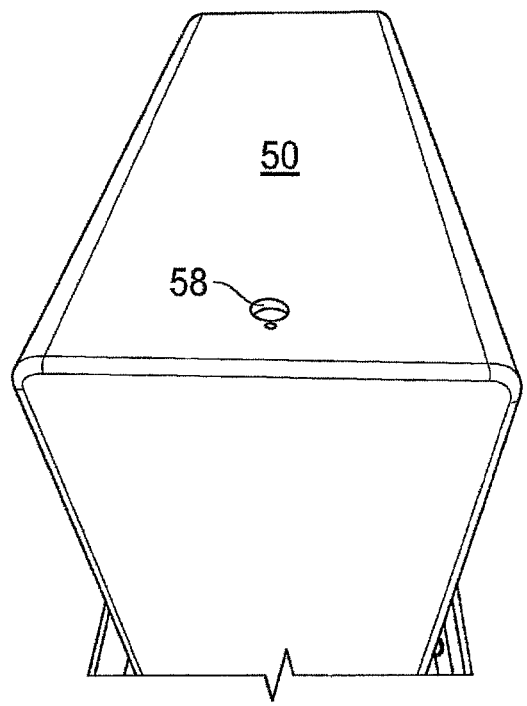
FIG. 10 is an enlarged underside view of the enclosure 50.

FIGS. 1 to 9 illustrate a lid mounted water sampling and testing system 10 adapted to be fluidly coupled to a water mains line (W) as shown in FIG. 3. The water sampling system 10 is provided for obtaining water quality parameters corresponding to a sample of pressurized water from the water line (W) and transmitting information associated with said water quality parameters to a remote location via a network (N). The system water sampling system 10 consists of a water sampling apparatus 12 that is mounted on an underside portion of a pit lid 11 that is adapted to cover an underground pit box 20. The pit lid 11 includes an outer (or in-use upper surface) 13 that comprises structural characteristics to allow the pit lid 10 to be tread upon or even driven upon. The pit lid 11 is adapted to be positioned to cover the pit box 20 such that during use the outer surface 13 of the pit lid 11 is substantially at ground level and adapted to be positioned upon the pit box 20 located underground.

The underside portion of the pit lid 11 is coupled to a water sampling apparatus 12. During use, the water sampling apparatus 12 is adapted to be positioned in an internal volume defined by the pit box 20 so that the water sampling apparatus 12 is not visible above ground level. Such a configuration allows, the water sampling and testing system 10 to be substantially hidden from plain sight. The aforementioned configuration also allows the water sampling and testing system 10 to be easily used in conjunction with conventional pit boxes (such as pit box 20) which are typically used for installation of water meters.

The water sampling apparatus 12 may include an inlet 14 that may be provided with quick coupling fittings to fluidly couple the water line (W) for obtaining water quality parameters corresponding to a sample of the pressurized water from the water line (W). A sampling valve 25 is provided in line with the water inlet 14 to control the flow of the flow (sampling flow) into the water sampling apparatus 12. The sampling valve 25 may be provided in the form of an electrically actuated solenoid valve in communication with a processing unit P. One or more water sampling programs may be stored locally on a non-volatile memory device M that communicates with the on board processing unit P. In some embodiments, the sampling valve 25 may be actuated from a remote location. By way of example, the processing unit P may be in communication with a data trans-receiver 15 that may receiving operation instructions from a remotely connected device via a network N.

The water sampling apparatus 12 includes a sampling line L that splits into a first sampling line L1 and a second sampling line L2. The first sampling line L1 that is coupled with the water line to allow water to flow from the water line to a dynamic pressure sensor $S_{TP}$ that is adapted to measure transient pressure at sampling rates across a wide range. For example, the pressure sensor $S_{TP}$ may measure transient pressure of water flowing through Line 1 ranging from say one reading every half an hour up to one reading every millisecond with a high degree of accuracy. The dynamic pressure sensor $S_{TP}$ is in communication with the on-board processing unit P which is in turn in communication with an on-board non-volatile memory unit M.

Figure 11:
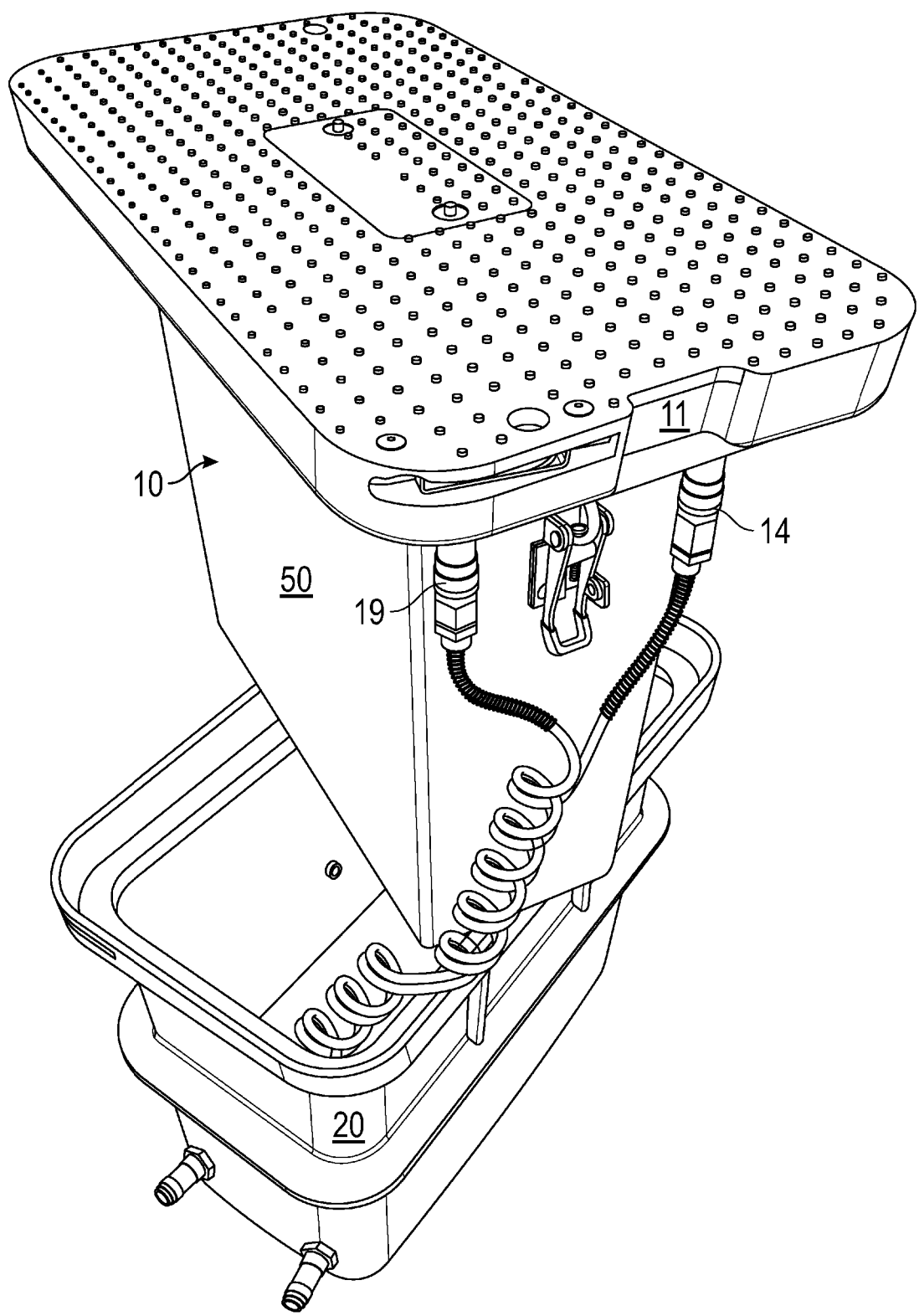
FIG. 11 showing the water sampling and testing system 10 shown in a coupled configuration whereby quick connect couplers couple inlet 14 with a water line and outlet 19 draining water away from the pit box 20.
Figure 12:
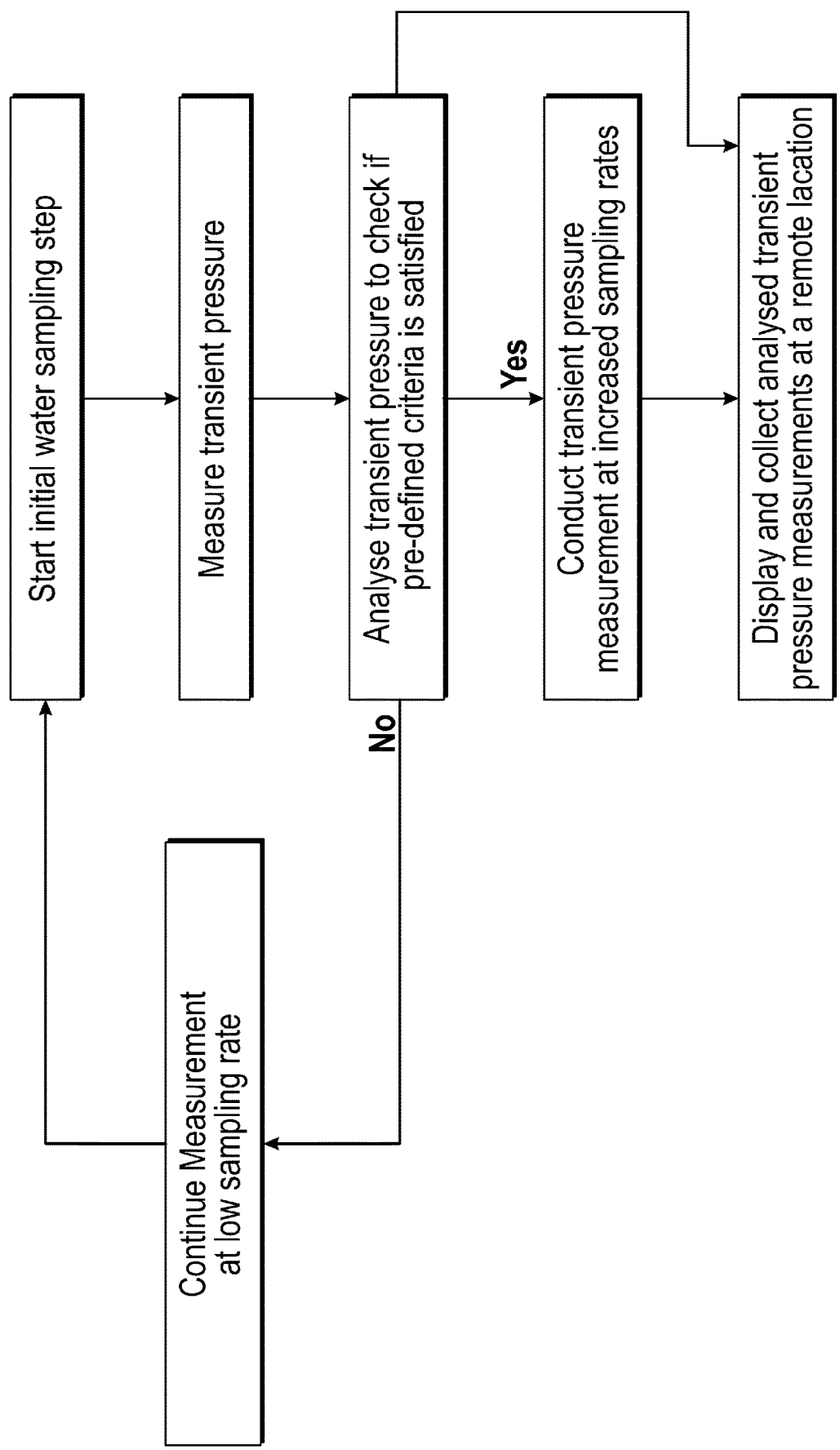
FIG. 12 shows stages of transient pressure detection using the dynamic pressure detector $S_{TP}$ (shown in FIG. 3).
Figure 13:
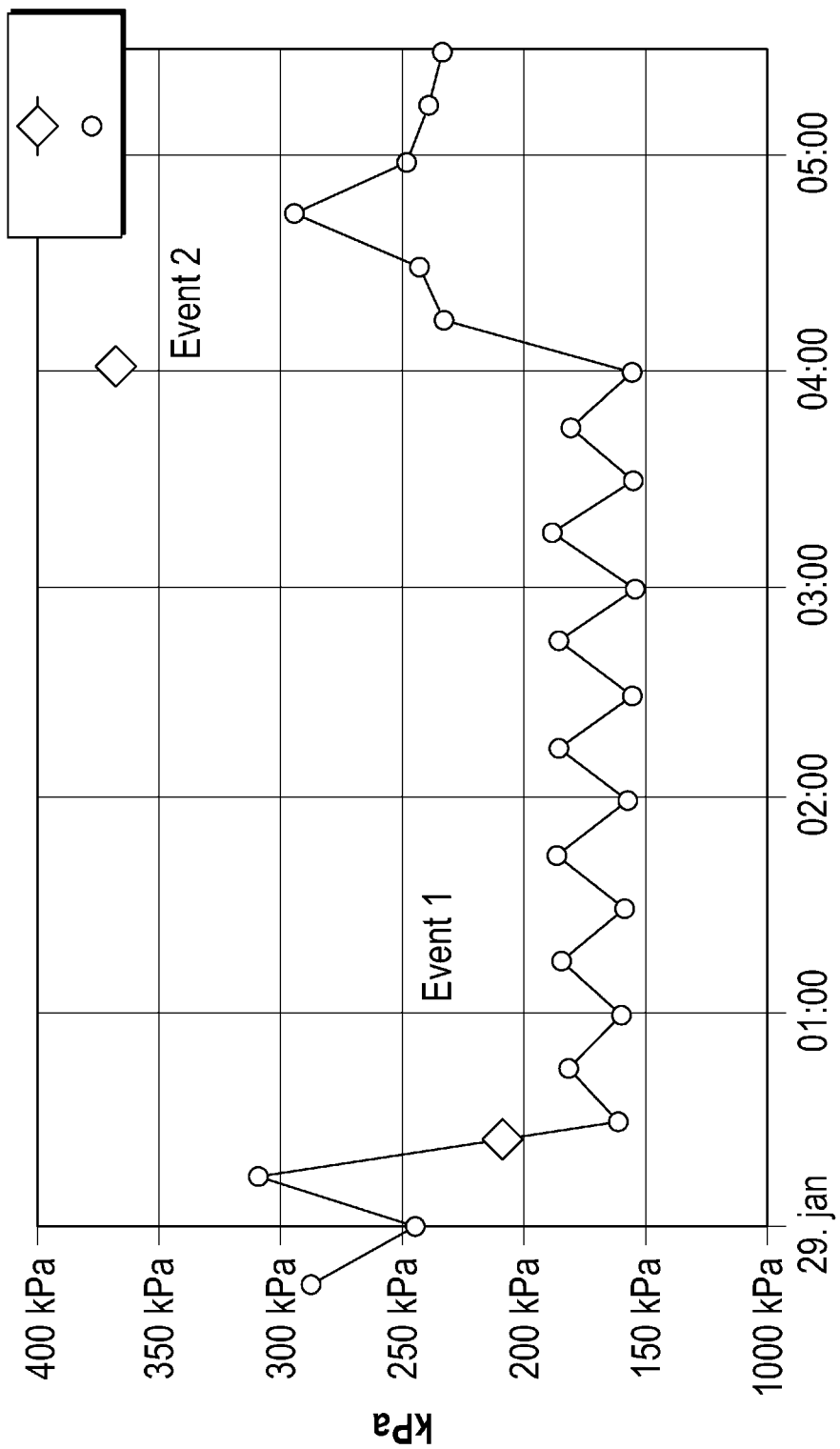
FIG. 13 is a graph of transient pressure versus time showing a dynamic pressure detection method (low sampling rate) with detected transient pressure events (Event 1 and Event 2).
Figure 14:
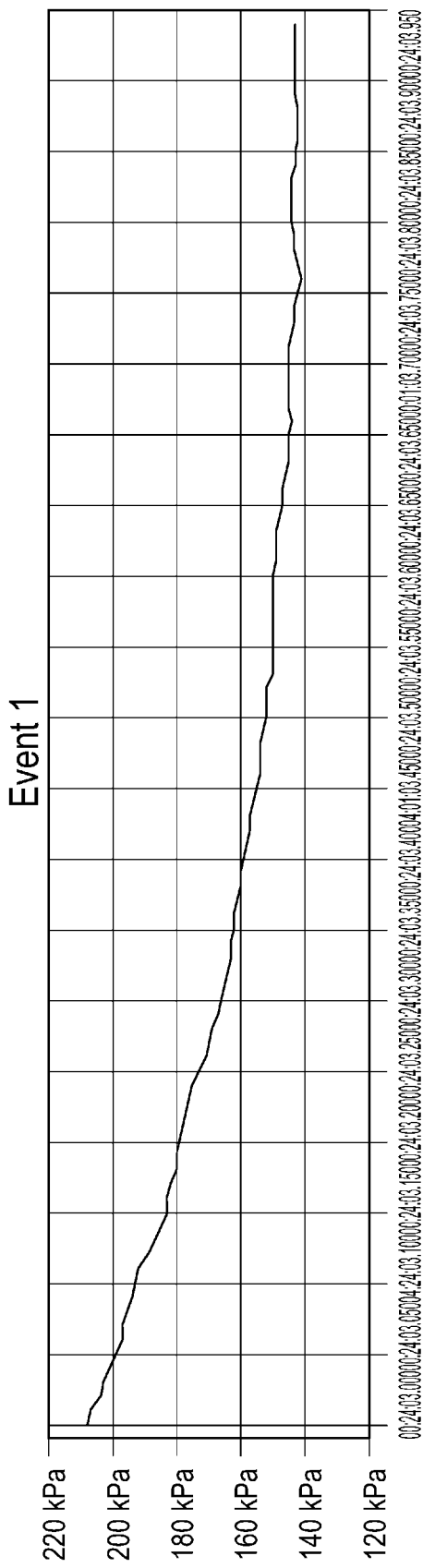
FIG. 14 shows transient pressure at a high sampling rate (every millisecond) during Event 1.
Figure 15:
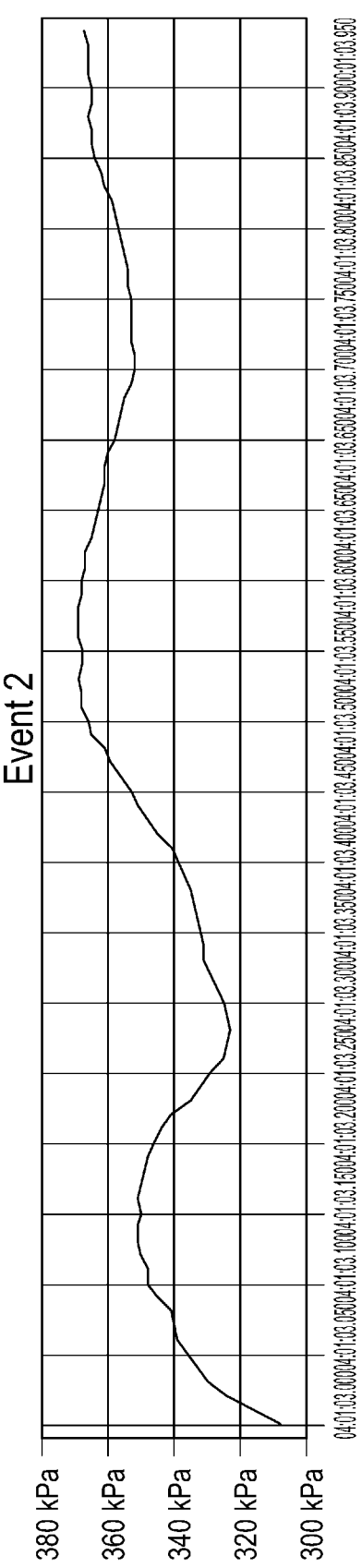
FIG. 15 shows transient pressure at a high sampling rate (every millisecond) during Event 2.

The dynamic transient pressure sensor $S_{TP}$ in combination with the on-board signal processing unit P identifies and processes the measured transient pressures based on user-defined parameters or criteria. During an initial sampling step transient pressure detection, data sampling rates remain constant, however, the data are all recorded in permanent storage and is preferably communicated and stored at a remote location for further retrieval and analysis. In a low power operating mode, measurements are taken and recorded at a relatively lower sampling rate. Referring to FIG. 11, a flow chart depicts a preferred method for operating the dynamic pressure sensor in the presently described embodiment of the water sampling system. The operator may program the on-board memory unit M to set the sampling rate at a pre-set parameter when the transient pressure meet a predetermined criteria. Each time, the transient pressure is measured by the dynamic pressure sensor $S_{TP}$, the on-board signal processing unit P processes the measured transient pressure parameters to assess if the predetermined criteria is satisfied. In one example shown in FIG. 13 a variation of transient pressure by over 100 kPa triggers an event (Event 1 and Event 2). It would be understood that such a criteria is not limited and a plurality of other predetermined criteria may be pre-set by the operator without departing from the scope of the present invention. Once an event is triggered, the on-board processing unit P communicates with a controller to increase the sampling rate. As shown in FIGS. 14 and 15, changes in transient pressure trigger measurement of transient pressure every millisecond thereby producing high resolution data only during times when an event has been detected. High frequency data detection and recordation continues until the pressure in the sampling line L1 returns to a steady state value that does not satisfy the predetermined criteria set by the operator. One of the non-limiting advantages of the present embodiment is that running the dynamic pressure sensor $S_{TP}$ at a low sampling rate when no events are detected, results in lower power consumption and less wear and prolongs the life of the dynamic pressure sensor $S_{TP}$. Such a measurement method also reduces the volume of measurement data that would need to be stored at the remote location on a storage device (such as a server). In short, a large number of data points during an event provide detailed insight into the nature of the transient pressure change when such detail is needed. Some of the most sever transient pressure changes may only last a few seconds and carrying out transient pressure sampling at a very high frequency over very long periods is impractical and the presently described water sampling system 10 addresses this issue in an elegant manner.

The second sampling line L2 is coupled with a plurality of sampling chambers S1 to S5 to direct water to flow from the water line to the sampling chambers S1 to S5. Each of the sampling chambers S1 to S5 includes sampling probes for measuring free chlorine concentration (probe 121), temperature (probe 122), oxidation reduction potential (probe 123), conductivity-$E_c$ (probe 124) and pH (probe 125) best shown in FIG. 6. Once the water has been sampled by the sampling probes associated with the sampling chambers S1 to S5, the sampled water may be released via an outlet 19. The outlet 19 may also be provided with quick coupling fittings to allow the outlet 19 to be coupled to a drainage line D (shown in FIG. 3). A pressure reduction valve 16 is provided in line with the second sampling line L2 for reducing the pressure of water entering into water sampling chambers S1 to S5. Water mains pressure in the mains water line (W) may be as high as 1000 kPa and the use of the pressure reduction valves 16 reduces the pressure to a lower pressure such as 350 kPa. The pressure reduction capacity of the valves 16 may be varied depending upon the required application. The reduction of the pressure using the pressure reduction valves 16 increases the residence time of water in each of the sampling chamber thereby improving sampling accuracy.

It is important to note that the use of the pressure reduction valve 16 must be limited to the second sampling line L2 and pressure must not be reduced in the first sampling line L1 which is used for monitoring changes in transient pressure. The novel configuration off the water sampling apparatus 12 allows the transient pressure and other important parameters such as chlorine concentration (probe 121), temperature (probe 122), oxidation reduction potential (probe 123), conductivity-$E_c$ (probe 124) and pH (probe 125) to be measure simultaneously. Transient pressure changes can occur because of a variety of reasons and changes in transient pressure alone do not provide conclusive detail on whether the changes have occurred due to mechanical reasons (such as opening or closing of valves) or whether there is a leakage which is in turn resulting in higher risk of contamination of water. For example, any leaks may give rise to negative transient pressure which can introduce contaminants into the water line. Measuring multiple characteristics along-with transient pressure by using the lid-mounted water sampling system 10 provides a higher level of detail to the operator and end user thereby improving the ability of operators to detect problems in the water line in a more efficient manner.

It is also important to note that the water sampling apparatus 12 includes a plurality of sampling probes in corresponding sampling chambers such as S1, S2, S3, S4, S5 which are adapted to sample water quality parameters of a sample of water being sampled. In the preferred embodiment, the multiple sampling probes 121 to 125 are connected in series such that water from the sampling line flows from one sampling chamber to another sampling chamber (in series) to carry out sampling of the water. Additional probes and additional sampling chambers may be used to measure one or more of the following parameters: hypochlorous-acid concentration; disinfectant residual; TC concentration; turbidity; Total Organic Carbon concentration; Total Chlorine concentration; Combined Chlorine concentration; Hydrogen Peroxide concentration.

Before entering into a description of the operation of the water sampling apparatus 12 shown in the figures, a brief discussion of ORP measurement is in order. ORP is a measurement of the electron exchange potential which occurs in an ionic reaction. Since most water distribution systems distribute ever-changing water, there typically is an undesired equilibrium created. The ORP measurement allows control of the electrochemical equilibrium.

The flow of water in mains is highly turbulent. Consequently, any contaminant rapidly forms a well-mixed "plug" that maintains its initial concentration for a time that is long compared with the time of residence in the pipes. In one scenario, the probes may detect a 30 mV or more rise or drop in redox potential due to the introduction of a contaminant. Scores of other harmful biological substances or live biological organisms would have a similar effect on redox potential, either by bulk reduction of the chlorine or by co-introduction of a chemical reducing agent that removes the chlorine shield and thus protects biological substances introduced at very low concentrations. The one or more probes may detect the loss of chlorination regardless of cause, which would allow the bloom of harmful microbes normally present in water or absorbed into the slime that coats the interior of water pipes.

The ORP probes may be non-specific thereby providing a broad response to the introduction of biological or chemical reducing agents into chlorinated water. The ORP probe in one embodiment may comprise a pair of electrodes: one is a Pt or graphite coated electrode; the other is a harmless reference electrode that is the type of an Ag/AgCl electrode used in medical procedures. The probes in various embodiments comprise a pair of electrodes that, under near-equilibrium conditions, output a potential proportional to the amount and strength of oxidizing material in the water. The potential or oxidation potential is not sensitive to the nature of the oxidant, and responds to all commonly used disinfectants including elemental chlorine, sodium hypochlorite, chloramines, chlorine dioxide, hydrogen peroxide or ozone, or even elemental oxygen. The ORP probes may be enhanced by combination with pH sensors, or specific ion electrodes for elemental chlorine or other toxic ions or compounds. The probes positioned in the sampling chambers S1 to S5 may operate as autonomous units. One or more of the sampling chambers S1 to S5 may measure redox potential of the sampled water and communicate water sampling data as outlined in the following sections.

The sampling probes positioned in the respective sampling chambers S1 to S5 are in signal communication with an on-board signal processor P which may be used for receiving and processing the measured water quality parameters (as measured by the one or more sampling probes). Operating and processing instructions for operating the sampling probes may be written onto the non-volatile memory device M that is communication with the processor P for allowing operation of the sampling apparatus 120. The data trans-receiver 15 communicates with the processing unit P and transmits the processed water quality parameters to and from the processor P via a network N to a remote server or computing device. In the preferred embodiment, the operation of the water sampling apparatus 12 is controlled or programmed from the remote server or computing device (preferably a cloud-based or web based interface) thereby allowing operating programs of the sampling apparatus 120 to be varied from a remote location.

Once the information related to the water quality parameters has been received at the remotely located server, the server may process the information in accordance with one or more pre-determined rules. By way of example, a rule may be saved onto the memory device M to check if the pH level of the sampled water is below a pre-determined threshold level. Similarly, another rule may be saved onto the memory device to check if the ORP of the sampled water is above or below a pre-determined threshold level. Similarly, a combination involving multiple rules may be saved on the memory device. Furthermore, these rules may be routinely changed from the remote location depending on the specific requirements of the water distribution and management system.

As previously described, the water sampling apparatus 12 may also measure changes in pressure over a period of time (known as 'transient pressure') in the water line W. A specific type of water related event may be detected by initially determining a predefined transient pressure wave signatures to set up a database and then matching those predefined signatures with actual transient pressure measurements. A transient pressure wave signature indicated by the output signal from the sampling apparatus 12 can be compared to the predefined transient pressure wave signatures that were stored or saved either on the memory device M or on the remotely located server. The previously described method of obtaining transient pressure values at a higher sampling rate when a predetermined transient pressure event is triggered can therefore be very useful.

The processor P and the memory device M may also be accessed from a remote location via the network N using a user input interface linked with the remote server or remote computing device to check the operating status of the sampling apparatus 12, change or manage sampling programs and configurations and update the operating firmware of the processor P.

The data trans-receiver 15 also comprises an antenna element A which is secured below the outer surface 13 of the pit lid 11. In the preferred embodiment, a top portion of the antenna element A (best shown in FIG. 2) is positioned adjacent to the underside of pit lid 11 for transmitting information associated with the measured water quality parameters to a remotely located computing device. Advantageously, the system is also provided with an on-board GPS unit G which communicates with GPS satellites G1 to G3 to indicate the geographical location of the water sampling and testing system 10. Positioning the antenna element A in close proximity to the pit lid 11 significant improves data transmission from the water sampling system 10 to remote locations. Similarly, positioning the GPS unit G in close proximity to the pit lid 11 improves location accuracy for the water sampling system 10.

The sampling chambers S1 to S5 are mounted onto a frame assembly 17 for detachably mounting the water sampling apparatus 12 in the underside portion of the pit lid 11. The frame assembly 17 allows the vertically oriented sampling chambers S1 to S5 to extend downwardly from the underside of the pit lid 11 thereby allowing the sampling apparatus 120 to be accommodated within the confines of the pit box 20.

It is to be understood that signal communication between the data transmitter 15 (over the network N) with the remotely located server or any other remotely located devices may be carried out through a cellular network, using networks such as GSM, GPRS, 3G 4G or 5G networks. The technology may also be configured to send and receive serial signal communications via one or more wireless or optical networks. The technology can also be configured to communicate with a remote device via an Ethernet connection, a 400-900 MHz radio, a microwave radio or a BLUETOOTH® device. Other signal connectivity methods may also be also be used to actuate the sampling valve 25 or transmit information from the sampling apparatus 12 to the remote location.

One of the many advantages for the presently described water sampling and testing system 10 is that the system can be located underneath ground level (shown in FIG. 2) whilst at the same time also provide information associated with water quality parameters to a remote location instantaneously without any delays. The compact and concealed configuration of the system 10 allows the system 10 to be easily installed in conjunction with pit boxes which are already used widely around the world.

Referring to FIGS. 7 to 11, the water sampling system 10 also includes an enclosure 50 for enclosing the water sampling apparatus 12. The enclosure 50 is preferably provided in the shape of a hollow cuboid (though other shapes may be provided without departing from the scope of the invention described herein) and includes a base located away from the pit lid 11 with upstanding walls of the enclosure 50 extending towards the pit lid 11 when in use. The upper portions of the upstanding walls are sealed against the pit lid 11 by using a sealing gasket 54. When sealed, the enclosure 50 provides an air pocket within which the water sampling apparatus 12 is housed. One of the potential issues with any electrical equipment mounted in a pit box 20 relates to sudden flooding or water logging which can invariably cause damage to the electronic componentry of the water sampling apparatus 12. The provision of the enclosure 50 that forms a seal to form an air pocket (within which the sampling apparatus 12 is housed) reduces the likelihood of damage being caused to the water sampling apparatus 12. Fastening clips 52 are provided to fasten the enclosure 50 to the pit lid 11 so that the sealed configuration of the enclosure 50 is maintained.

The enclosure 50 is also weighted (for example by using weight members 56) by to make the combination of the pit lid 11, the water sampling apparatus 12 and the enclosure 50 negatively buoyant when the combination is submerged in water that fills up in the pit box 20. The negatively buoyant combination of the pit lid 11, the water sampling apparatus 12 and the enclosure 50 pushes against the rim of the pit box 20 thereby preventing the combination from popping up and floating on water during a flooding event. A draining outlet 58 is also provided in the base of the enclosure 50 to allow water drain out of the enclosure in case there are small leaks or water accumulation (due to condensation) within the enclosure 50. The air inside the sealed enclosure 50 prevents any water from entering through the outlet 58. The outlet 58 is sized and located to ensure that even as the water pressure rises (due to increasing water levels), the water pressure compresses the air inside the enclosure 50 even more. However, since the air inside the sealed enclosure 50 cannot escape the air continues to take up the volume within the enclosure 50 thereby preventing water damage to the water sampling apparatus 12. In addition the pressure reduction valves 16 regulate the pressure of the water to be above a pressure of 101.35 Kilopascals and preferably in a range between 137 Kilopascals and 206 Kilopascals such that any water leak which may develop at any time from any part of the water sampling apparatus 12 which is inside the enclosure 50 will occur at a pressure above atmospheric pressure of 101.35 Kilopascals. As a result, any water leaking into the enclosure 50 will therefore pass through the outlet 58 to either the atmosphere outside the enclosure 50, or where the enclosure 50 itself is surrounded by water, then it will pass into to the surrounding water in the pit box 20.

In compliance with the statute, the invention has been described in language more or less specific to structural or methodical features. The term "comprises" and its variations, such as "comprising" and "comprised of" is used throughout in an inclusive sense and not to the exclusion of any additional features.

It is to be understood that the invention is not limited to specific features shown or described since the means herein described comprises preferred forms of putting the invention into effect.

The invention is, therefore, claimed in any of its forms or modifications within the proper scope of the appended claims appropriately interpreted by those skilled in the art.

What is claimed is:

1. A lid-mounted water sampling system adapted to be fluidly coupled to a pressurized water supply line for obtaining water quality parameters corresponding to a sample of pressurized water from the pressurized water supply line and transmitting information associated with said water quality parameters to a remote location, the system comprising:
   a pit lid adapted to be positioned to cover an opening of a pit box such that during use an outer surface of the pit lid is substantially at ground level and adapted to be positioned upon the pit box located underground;
   the pit lid further comprising an in-use underside portion coupled to a water sampling apparatus, the water sampling apparatus adapted to be positioned in an internal volume defined by the pit box, the water sampling apparatus being fluidly coupled to the water line for obtaining water quality parameters corresponding to a sample of the pressurized water, pressurized above 101 kilopascals, from the pressurized water supply line;
   one or more connectors arranged relative to the underside portion of the pit lid for coupling the water sampling apparatus to the pressurized water supply line such that the lid-mounted water sampling system is adapted to be readily uncoupled from the pressurized water supply line;
   a frame assembly for mounting the water sampling apparatus in the underside portion of the pit lid, the frame assembly being coupled to the underside portion of the pit lid; and
   a data transmitter positioned adjacent said pit lid in electronic communication with the water sampling apparatus for transmitting the water quality parameters to the remote location.

2. A lid-mounted water sampling system in accordance with claim 1 wherein the water sampling apparatus is adapted to measure one or more of the following parameters:
   (a) transient pressure;
   (b) temperature of water;
   (c) pH of water;
   (d) oxidation reduction potential (ORP);
   (e) Conductivity (EC); and
   (f) Free Chlorine concentrationt.

3. A lid-mounted water sampling system in accordance with claim 1 further comprising: a first sampling line for being coupled with the water line for allowing flow of water from the water line to a dynamic pressure sensor to measure the transient pressure in the water line; and a second sampling line for being coupled with the water line for allowing flow of water from the water line to a plurality of sampling chambers with corresponding sampling probes, the sampling probes being adapted to sample water quality parameters of a sample of water flowing into said sampling chambers.

4. A lid-mounted water sampling system in accordance with claim 3 wherein the dynamic pressure sensor is arranged to conduct an initial water sampling step to identify transient pressure in the water line and transmitting transient pressure related information to a receiver and a signal processor, said signal processor being arranged to receive and process transient pressure related information to determine if transient pressure in the water line satisfies a pre-determined criteria, the signal processor being in communication with a control unit to undertake one or more additional water sampling steps when the pre-determined criteria is satisfied.

5. A lid-mounted water sampling system in accordance with claim 4 wherein the control unit is arranged to operate the water sampling system in a low power consumption operating configuration when the pre-determined criteria is not satisfied.

6. A lid-mounted water sampling system in accordance with claim 4 wherein the control unit is programmed or programmable to increase water sampling rates or data recording rates when the predetermined criteria is not satisfied.

7. A lid-mounted water sampling system in accordance with claim 1 wherein the water sampling apparatus further comprises a sampling valve to control the flow of water from the water line into the first and second sampling lines.

8. A lid-mounted water sampling system in accordance with claim 7 wherein the sampling valve is in electrical communication with a data trans-receiver for allowing remote actuation of the sampling valve.

9. A lid-mounted water sampling system in accordance with claim 7 wherein the sampling valve is in electrical communication with a processor to execute sampling instructions written onto a non-volatile memory device arranged in communication with a processor by actuating said sampling valve in accordance with said sampling instructions.

10. A lid-mounted water sampling system in accordance with claim 3 wherein the water sampling apparatus further comprises a pressure reduction valve positioned in fluid communication with the second sampling line for reducing pressure of water flowing from the water line into the plurality of water sampling chambers.

11. A lid-mounted water sampling system in accordance with claim 1 wherein the transmitter further comprises an antenna element secured relative to the pit lid wherein a top portion of the antenna element is positioned adjacent to the underside of pit lid for transmitting information associated with said water quality parameters to the remote location.

12. A lid-mounted water sampling system in accordance with claim 1 wherein the data transmitter for transmitting the water quality parameters to a remotely located processing unit is configured to receive and process the water quality parameters for the one or more samples sampled by the sampling apparatus in accordance with one or more water quality parameters processing instructions written onto a remotely located non-volatile memory unit in communication with said remotely located processing unit.

13. A lid-mounted water sampling system in accordance with claim 1 wherein the data transmitter is adapted to be in wired or wireless communication with a remote server.

14. A lid-mounted water sampling system in accordance with claim 1 further comprising an on-board processing unit in communication with the water sampling apparatus and the data transmitter for processing and transmitting information associated with said water quality parameters to the remote location.

15. A lid-mounted water sampling system in accordance with claim 1 further comprising: an enclosure for enclosing at least a part of the water sampling apparatus with a sealing arrangement, the sealing arrangement being provided to form a seal between the enclosure and the pit lid and/or the water sampling apparatus.

16. A lid-mounted water sampling system in accordance with claim 15 wherein the sealing arrangement is located at an in-use upper section of the enclosure that forms the seal between the enclosure and the pit lid and/or the water sampling apparatus.

17. A lid-mounted water sampling apparatus in accordance with claim 15 wherein the enclosure in combination with the water sampling apparatus and/or the pit lid is negatively buoyant to prevent the combination of the pit lid, water sampling apparatus and the enclosure from becoming buoyant when submerged in water.

18. A lid-mounted water sampling apparatus in accordance with claim 15 wherein the enclosure further comprises an outlet opening to allow water from inside the enclosure to be discharged outside the enclosure.

19. A lid-mounted water sampling apparatus in accordance with claim 18 wherein the outlet is positioned in an in-use lower section of the enclosure.

20. A lid-mounted water sampling apparatus in accordance with claim 18 wherein the enclosure comprises a base forming the in-use lower section of the enclosure with upstanding walls extending from the base in a direction towards the pit lid, the outlet being positioned in the base of the enclosure.

21. A lid-mounted water sampling apparatus in accordance with claim 1 further comprising a sampling pressure regulator to regulate the pressure of water flowing through the water sampling apparatus to be in the range of 130 kilopascals and 210 kilopascals.

22. A method of sampling water, the method comprising the steps of:
  positioning a water sampling apparatus below an underside portion of a pit lid, the pit lid being adapted to be positioned to cover an opening of a pit box such that during use an outer surface of the pit lid is substantially at ground level and adapted to be positioned upon the pit box located underground;
  mounting the water sampling apparatus in a frame assembly and coupling said frame assembly to the underside portion of the pit lid,
  fluidly coupling one or more connectors arranged relative to the underside portion of the pit lid to said water sampling apparatus to sample pressurized water, pressurized above 101 kilopascals, from a pressurized water supply line for obtaining water quality parameters corresponding to a sample of the pressurized water from the water line;
  transmitting the water quality parameters, by a data transmitter positioned adjacent said pit lid, to a remote location.

* * * * *